United States Patent [19]

Weisberg

[11] 3,985,853
[45] Oct. 12, 1976

[54] METHOD OF MAKING A COMBINED HEEL POSITIONER AND ARCH SUPPORT FOR THE FOOT

[76] Inventor: Alex Weisberg, Beverly Hills, Calif.

[22] Filed: Oct. 14, 1975

[21] Appl. No.: 621,873

Related U.S. Application Data

[62] Division of Ser. No. 506,392, Sept. 16, 1974, Pat. No. 3,927,140.

[52] U.S. Cl. .............................. 264/250; 264/223; 264/251; 264/266; 264/267; 264/294; 264/313; 264/45.1; 264/46.4; 264/46.6
[51] Int. Cl.² ........................ B29D 9/00; B29G 7/00
[58] Field of Search ............... 128/586, 594, 595; 36/44; 264/259, 236, 250, 251, 254, 261, 266, 267, 294, 313, 331, 46.4, 46.5, 46.6, 45.1

[56] References Cited
UNITED STATES PATENTS

| | | | |
|---|---|---|---|
| 2,123,730 | 7/1938 | Huttleston | 128/595 |
| 2,546,827 | 3/1951 | Lavinthal | 128/595 |
| 2,762,134 | 9/1956 | Town | 128/594 |
| 3,121,430 | 2/1964 | O'Reilly | 128/595 |
| 3,782,390 | 1/1974 | Johnson | 128/595 |
| 3,892,077 | 7/1975 | Wolstenholme et al. | 36/71 |
| 3,905,376 | 9/1975 | Johnson et al. | 128/595 |

Primary Examiner—Willard E. Hoag
Attorney, Agent, or Firm—I. Morley Drucker

[57] ABSTRACT

A method of making an insole having a heel positioner and an arch support, in which the positioning support for the heel is made in situ, in one discrete section of the foot support, and the arch support is then made, in situ, in a second discrete section.

The first discrete section is made at the heel portion of the foot, in a manner so as to stabilize the plantar surface of the heel section of the foot under the cancaneous bone. This is for the purpose of eliminating, reducing or minimizing the rotation forces applied to the heel section of the foot by the weight of the body, which would normally tend to produce a pes valgus (outward bending) or a pes varus (inward bending) condition, as well as stabilizing the anterior-posterior position of the leg in its function of bearing body weight.

Once the heel stabilizer section has been formed, in situ, a discrete arch support section is then provided, in situ, for the arch portions of the foot so that the body weight will not tend to place strain upon the inner structures of the foot (bone joints, tendons, muscles, and related tissues), in the arch sections which connect the heel to the second part of the foot that support the body weight (i.e., the ball of the foot).

13 Claims, 4 Drawing Figures

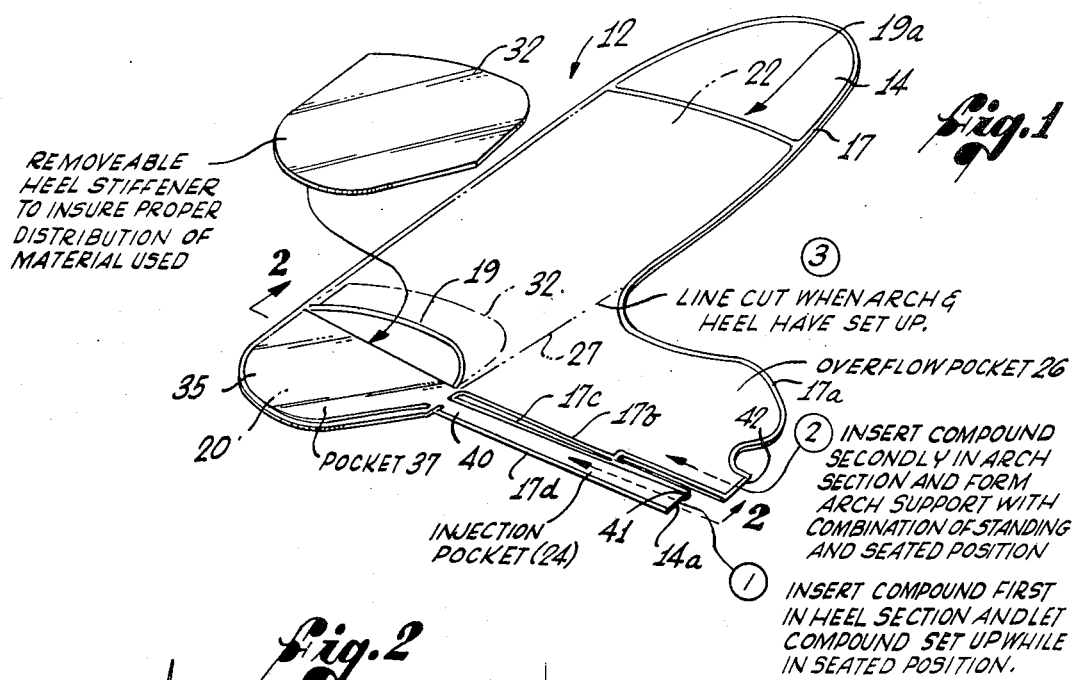
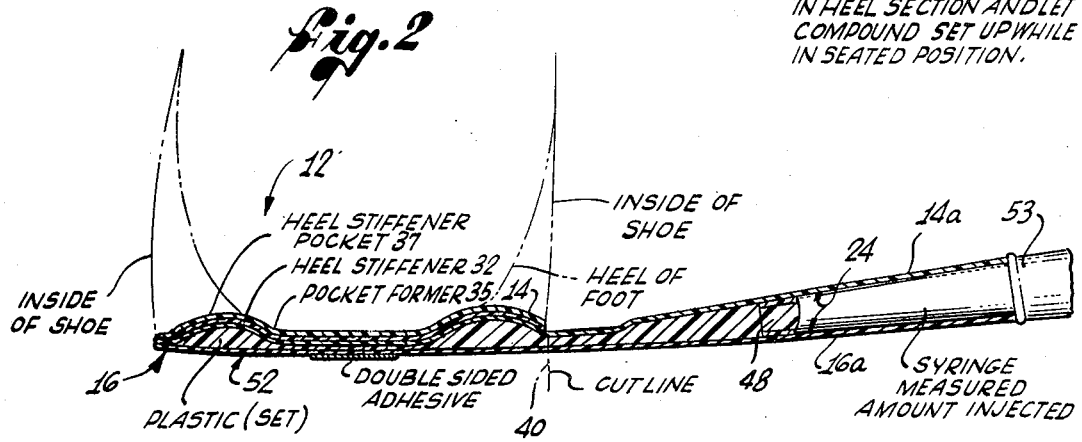
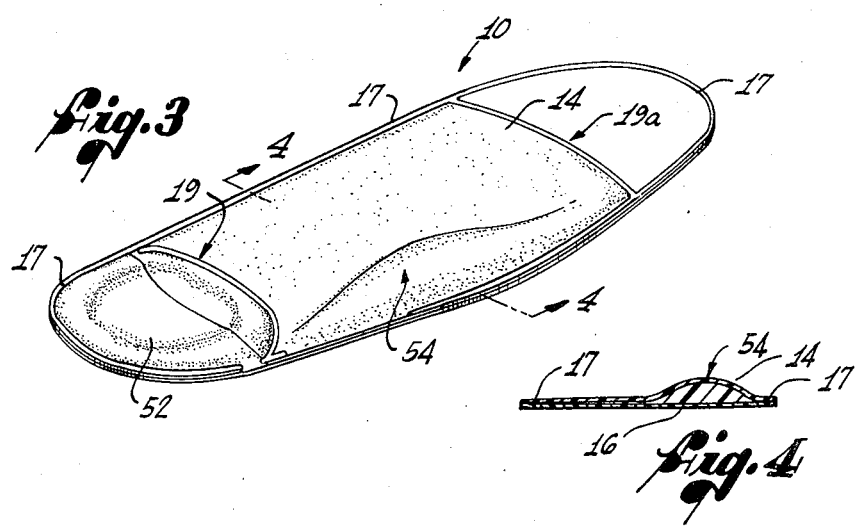

METHOD OF MAKING A COMBINED HEEL POSITIONER AND ARCH SUPPORT FOR THE FOOT

CROSS REFERENCE TO RELATED APPLICATION

This application is a division of Ser. No. 506,392, filed Sept. 16, 1974 and now U.S. Pat. No. 3,929,140.

INTRODUCTION

The necessity for an arch support is well covered in the literature. To quote from "Orthopedic Appliances, by Henry H. Jordan, Oxford University Press 1939", an arch support is used "to effect a correct, painless distribution of the weight to establish as far as possible the correct position of the elements of the foot in relation to the line of gravity of the leg".

Many individuals believe that an arch support should be formed in the shoe that it is to be worn with, so as to match simultaneously both the plantar surface of the foot and the inner sole of the shoe. The major purpose of my invention incorporates improved methods and means over those previously proposed and used, to effect a proper balanced foot support for those individuals that need and desire to use one. The invention is directed to a method and means of effecting proper distribution of body weight upon the plantar surface of the foot, with minimal strain, stress and distortion to the inner structures of the foot.

It is well documented in medical literature that proper positioning and support of the feet leads in turn to the correct positioning of the legs, knees, thick, and back of the individual with resulting greater comfort in these areas.

Theoretically, in a normal standing position, the weight born by a foot is divided approximately between the heel and the ball of the foot. However, the heel bone of the foot is in a more direct line with the skeleton of the leg, and thus bears most of the actual total weight, with the ball of the foot and the connecting arch structures serving mainly a balancing function.

The stability and position of that part of the foot under the heel bone is most important in controlling the supination and pronation positions of the foot, as well as anterior - posterior stabilization of the leg. The ability to prevent involuntary supination or pronation and to provide proper anterior - posterior stabilization leads to a more vertical position of the leg and thus to a more normal position of the body as a whole.

Heel wedges, orthopedic heels, and other methods are generally used to position the heel bone and obtain proper support in the heel area. However, these methods are inaccurate. A method and means which permits an in situ heel positioning is believed to be much more accurate.

It is known, that in order to construct an arch support within a shoe, with the foot in the shoe, a hydraulic system may be used. By this, it is meant that an initially flowable material enclosed within a chamber is placed under the plantar surface with the foot in the shoe in order to flow under pressure and distribute itself in a pattern that is determined by the contour and pressures of the plantar surface against this material. The initially flowable material then sets or cures to the desired configuration required to support the plantar surface in an optimum manner.

Experiments with an insole device comprising a single chamber for acceptance of a settable fluid system showed that due to the great amount of weight under the heel bone little or no material remained in this critical heel area when the proper and sufficient amount of material was obtained in the arch system of the foot. This type of approach is perhaps best exemplified by O'Reilly, U.S. Pat. No. 3,121,430.

Consequently, the single chamber approach of O'Reilly did not prove to be satisfactory. With this in mind, it was a major object of this invention to provide proper balance and support of the foot by first properly positioning and comfortably supporting the heel portion of the foot by a first discrete heel support section, formed in situ, and then forming, in situ, a second discrete section for support of the arch portion of the foot.

SUMMARY OF THE INVENTION

This invention is specifically directed to the formation of a dual chamber insole, in situ, the dual chambers comprising, in general terms, a discrete heel positioning support chamber and a discrete arch support chamber.

Inlets for the introduction of room temperature settable fluids, e.g., silicones, into each of the chambers is provided. Room temperature settable fluids are designated in the trade as room temperature vulcanizing (RTV) compounds. In situ molding to the heel and arch of the wearer are made as follows. The heel positioner and support is formed, in situ, by injecting RTV fluids into the discrete heel positioner section. While the insole support envelope is in place between the foot of the user and the inner surface of the shoe, the user remains in seated position, with his body weight off the foot, while the positioner and support is being formed. In this way, the heel positioner and support may be properly formed without undue displacement of settable material.

After curing of the settable material in the heel section, the second support chamber is injected with a measured amount of the same settable plastic fluid. While the user is in standing position with his weight on the envelope. The fluid on setting will conform to the plantar surface of the wearer, the conformity, however, being of an optimal nature, however, due to the proper positioning of the heel by the heel support section.

BRIEF DESCRIPTION OF THE DRAWINGS

FIG. 1 is a top plan view, in perspective, of the insole support envelope of my invention, showing the various chambers therein. The insole envelope is shown prior to the introduction therein of settable fluids for foot support purposes and prior to its insertion into the left shoe of a user;

FIG. 2 is a cross-sectional view of the insert envelope of FIG. 1, taken along line 2—2 at a time after introduction of RTV fluid into the heel support section of my insert support envelope;

FIG. 3 is a perspective view of the finished insole support of my invention; and FIG. 4 is a cross-sectional view of insole support taken along the line 4—4 of FIG. 3.

DETAILED DESCRIPTION OF THE PREFERRED EMBODIMENT

The insole support of my invention, shown in FIG. 3 and designated by the numeral 10 is made, in general, by injecting RTV fluids into dual chambers formed in an insert support envelope, the insole support envelope for the left foot being shown in FIG. 1.

The insert support envelope of FIG. 1 is designated generally by the numeral 12. The envelope 12 is provided with an upper panel or layer of a preferably fabric-lined plastic sheeting 14, the fabric lining (not shown) being internally mounted to the sheeting 14. The sheeting 14 may comprise, by way of example, a fabric backed (or lined) vinyl or a fabric backed polyurethane of suitable thickness and flexibility, the purpose of the fabric lining being to provide a mechanical bond between the fabric of sheeting 14 and the cured RTV plastic.

The bottom panel or layer 16 of the insert support envelope 12 comprises a preferably transparent, plastic sheet of flexible polyvinyl chloride or polyurethane, that is readily welded to upper panel 14 along peripheral weld lines 17 and internal weld lines 19, 19a. The internal and peripheral weld lines 17, 19, 19a form a heel positioner and support chamber 20 and an arch support chamber 22, respectively.

An injection pocket 24 is also provided in communication with heel support chamber 20, through neck 40, the injection pocket 24 being preferably formed of a pair of superposed layers 16a and 14a which are merely medial continuations of layers 16 and 14, respectively.

An overflow pocket 26 is provided which communicates only with arch support chamber 22, through an opening coinciding with the dotted line 27. The overflow pocket 26 and its inlet port 42 are preferably formed as part of insert support envelope 12, and the upper and lower panels or layers constituting the overflow pocket 26 and inlet port 42, are thus medial continuations of the upper and lower layers 14 and 16, respectively.

The welding of upper and lower sheets or panels, 14, 16 is readily performed by conventional dielectric sealing means. The lower panel 16 forming the insert support envelope is approximately 10–15 mils in thickness and it is also presently preferred that the inner surface thereof have a textured configuration. The textured surface aids the flow characteristics of the presently preferred settable fluid, (which is a room temperature vulcanizing (RTV) silicone) during formation of the insert support, and also will impart a textured finish to the cured silicone layer of the finished product — which will aid in maintaining this insert support in place when worn in the shoe.

The top layer 14 of the insert support envelope 12 is preferably provided with a removable heel stiffener 32. The heel stiffener 32 comprises a fairly rigid plastic piece, e.g., made of polyvinyl acetate of about a 20 mil thickness. The heel stiffener 32 is positioned over the heel support chamber 20 by means of a stiffener pocket 37. The pocket 37 is formed simply by dielectric welding a flexible vinyl sheet 35 of perhaps 10–12 mils in thickness along the periphery of the heel support chamber 20 only. The stiffener 32 extends forwardly of the stiffener pocket 37 so formed. The detailed purpose of the heel stiffener 32 will be later described.

The periphery of the insert support 10, formed by weld line 17, is such as to preferably form a finished insert support which approximates the innersole area of the shoe to be fitted.

The peripheral welds along lines 17d, 17c, 17a and 17b form a flexible injection port 41 to chamber 20, a flexible overflow pocket 26 and a flexible injection port 42 to chamber 22, respectively. The heel positioner chamber 20 is formed by weld line 19 which line runs approximately below the line of insertion of the spring and long plantar ligaments into the calcaneous (heel) bone. The arch support chamber 22 is formed by weld line 19 and by anterior weld line 19a which is in the ball area of the plantar surface.

The injection pocket 24 (and its entrance port 41 and neck 40) together with overflow pocket 26 (and its entrance port 42) are sometimes referred to generally hereinafter, and in the claims, as first and second flexible conduit means extending medially with respect to the heel support and arch support chambers, respectively. These first and second conduit means each preferably have a length in excess of the height of the shoe measured from the insole to the upper edge of the shoe in order to avoid any overflow of material into the wearer's shoe.

The upper and lower layers 14, 16 of envelope 12 preferably extend anteriorly of weld line 19a, in order to cover the full inner sole of the shoe - as an additional means of maintaining the insole support 10 of this invention in place. It is not a requirement, however, and the support insert 10 could terminate anteriorly along line 19a.

The envelope 12 may be cut between weld lines 17b and 17c to facilitate independent manipulation of the entry ports 41 and 42 to chambers 20, 22.

The neck 40 of the injection pocket 24 is proportioned so that the nozzle 48 of an injection syringe 53 can be tightly wedged into the neck 40 while injecting the settable plastic mix into the heel support chambers 20. The neck 40 of the heel chamber 20 thus preferably narrows to a diameter of not more than ½ inch. The purpose of this "necking down" is to minimize the escape of any RTV fluid material from the heel chamber 20 during the formation and setting of the heel support section.

The amount of RTV settable fluid injected into the heel chamber 20 is based on a numerical formula relating volume to heel chamber area to be later set forth herein. Further, during the actual setting of the material in the heel chamber 20, the injection pocket 24 is turned up inside the shoe of the wearer, and material outflow through neck 40, is greatly inhibited. Moreover, the heel stiffener 32 prevents outflow of material through the neck 40 by offering a barrier or dam to any outflow through neck 40.

The overflow pocket 26, in contrast, communicates with arch support chamber 22, by means of a very wide neck indicated, generally, by dotted line 27. Excess RTV fluid can thus readily escape from chamber 22 during the molding operation of the arch support.

Both chambers 20, 22 together with their respective flexible conduit means, are open systems for the purpose of placing the RTV fluid into these chambers, and at the same time, allowing any air trapped in the chambers 20, 22 to be expelled. In this connection, it is found advantageous to manipulate the RTV plastic fluid once it has been placed into the chambers 20, 22 in such a manner as to collect the trapped air and to expel this air out of the chambers 20, 22 through the ports 40, 41, 42.

MATERIALS EMPLOYED

The preferred room temperature settable material at this time is one of a series of silicone rubber compounds manufactured by General Electric Company, Silicone Products Department, Waterford, New York 12188.

These room temperature vulcanizing (RTV) silicones are preferably two-part compounds, such as General Electric's RTV-1041 (wherein the preferred curing agent is General Electric's CS 4097C or CS-4096C). Other successfully employed compounds include General Electric's RTV 11 and RTV 1012. Other materials of choice are found in GE's Technical Data Book S-35 and Product Data on Silicone Dental Moldings and Formulating Compounds (Bulletin No. CDS-316).

The use of a silicone rubber has the following major advantages:

1. it is physiologically inert;
2. after mixing and setting, it has very poor adhesive qualities, especially to plastics, leather and skin. This makes clean up of excess and spilled material very easy.
3. it is easy to repair or add to the cured material. A new mix will bond to an old one.
4. Mechanical bonding is simple and strong. This is the reason for the fabric backing to the upper layer of the envelope.

Other materials, such as a two part polyurethane base and catalyst system may also be used but at the present state of the art, it is a more sensitive and difficult material to use than the silicone materials.

PROCEDURE

1. Place a strip of two sided adhesive tape 40 on inner side of each shoe to hold the insert support envelope 12 in place during the setting period.

2. Place the plastic stiffener 32 into pocket former 37 of each insert support envelope 12.

3. Dispense a predetermined amount of a settable fluid such as an RTV silicone rubber base compound into a large syringe (a sufficient quantity being that required for two heel chambers 20). The amount to be dispensed into each chamber should be approximately ½ cc per sq. cm of the finished heel chamber 20. However, this amount is somewhat variable and will depend upon the configuration of the insole of the shoe being fitted and the amount of heel positioning correction that may be desired.

4. Fill a small calibrated syringe (not shown) with a desired curing agent in a ratio of about 1/10 amount of the silicone compound placed in large syringe.

5. Inject the contents of small syringe into the large syringe 53.

6. Mix thoroughly with a spatula (not shown) for approximately one minute. Thorough mixing is important to obtain a proper set.

7. Screw a plastic nozzle 48 onto the syringe 53 and while holding syringe with the nozzle up, expel trapped air from syringe and nozzle.

8. Insert the nozzle 48 into the injection pocket 24 of the heel support chamber 20 and expel the predetermined amount of mix into chamber 20, as measured by the calibrations on the syringe 53.

9. Repeat Step 8 to fill the heel support chamber 20 for the other insert support envelope.

10. For each insert support envelope 12, all of the material is manually forced away from the neck 40. This will result in trapped air being forced toward the neck 40, and the air bubble is then forced out through the neck. The procedure is repeated 2 or 3 times, to make sure all air is removed.

11. After all air is removed, bend over the ends of each injection pocket 24 and close them off by clamping spring clips (not shown) onto the openings of the injection pockets.

12. Place the envelope 12 in their respective shoes, holding the same in proper position with the two sided adhesive strip 40. The entrance ports 41 always face medially, that is, toward the opposite foot.

13. Place each foot in the proper shoe and lace same. This must be done in a sitting position. Total body weight should never be placed on the envelope 12 while the heel section is being formed. There is a slight danger of breaking the plastic welds 17, 19, 19*a* and forcing the mix onto the shoe, and more importantly, there is no control over the flow of the material that is required in order to obtain the proper configuration necessary to obtain the correct heel support (position and stability).

14. The setting time of the silicone is approximately 15 minutes from the time the curing agent is incorporated into the compound. About ½ of this time (approximately 7 to 8 min.) is allowed for the above steps 5 through 13.

15. In a sitting position, the feet are placed together with the legs vertical. This position must be maintained for approximately another 7 to 10 minutes. The time can be determined by watching and testing a small quantity of the mixed material until it reaches a tack-free consistency.

16. The position of the feet together and the legs vertical (the leg being that portion of the anatomy between the knees and ankles) is the position to be used for an individual that does not require any major correction of the foot position. If there is a need to add correction to the pattern of the compound, it can be done by positioning the leg and foot (keeping the sole of the shoe flat upon the floor) in a position that is opposite to the condition for which correction is desired. Thus, for example, if a pronated foot, or pes valgus, exists and a correction is desired then the leg and foot should be placed so that a position of supination, or pes varus, is maintained during the setting period of the settable fluid, e.g., the silicone mix. Corrections such as this and others that may be required should generally be prescribed by an orthopedic physician or a podiatrist.

17. When the sample of the mix shows that it has set the shoes are removed, and the envelopes 12 taken out.

18. The heel stiffeners 32 are then removed. The purpose of the heel stiffener 32 is to prevent undue displacement of soft tissue areas of the heel, particularly on the peripheries thereof, and especially on the mesialanterior corner of the heel area, by the hydraulic pressures exerted by the silicone material itself. The stiffener 32, which may be of about 20 mil in thickness, is still sufficiently flexible to allow proper distribution of the silicone material, while preventing undue build up and displacement in any particular area. The pattern of the rigid stiffener is such that it will preferably extend anterior to the border of the heel chamber 20, again to prevent excess material from collecting in the mesial-anterior corner. It is possible, also, to eliminate the heel stiffener 32 entirely by making the heel section of layer 14 of a more rigid material while maintaining the arch support section of a more flexible nature.

19. Repeats Steps 3 through 12, and fill arch support chambers 22 of each envelope 12. The amount of material is not critical but an excess is desired and provided for by the overflow pocket 26. Approximately 2 to 3 times the quantity of material used in the heel chamber will be required. This will vary and depend upon the shape and type of shoe, the height of the individual's arch, and any correction that may be desired. Also, before placing the envelopes 12 into the shoe all of the fluid is forced to the lateral wall (away from the entrance port 42). This will aid the flow characteristics of the material, and will also aid in the expulsion of any air not previously removed.

20. With the envelopes 12 properly placed in the shoes, and the feet into the shoes, they are laced and the person is placed in a normal standing position with the legs vertical and feet together (or nearly so). This position is to be maintained for about 2 to 3 minutes and should not exceed the flowability time of the mix. In this period of time the mix will flow into those areas of the arch section of the plantar surface that are not receiving support from the shoe structures and all excess material will go into the overflow chamber 26. The foot is not flexed nor is any pressure applied, as by walking, during this period. Due to the previous correction in the heel chamber 20, the leg will be in a more normal vertical position with little or no tendency for abnormal or improper positioning, such as pronation or supination, and thus the fluid in the arch chamber will flow in such a pattern as to support the arches (both longitudinal and transverse) in a more normal position for the given individual wearing the shoes being fitted. However, if correction is desired, the foot and leg should be positioned as outlined in Step 16. Correction can be placed into either the heel portion or the arch portion, or both, depending on the existing foot deformity.

21. While the material is still in a flowable state, the person should sit down with the legs and feet in the same position as described in Steps 15–16. The reason for this is to allow for the relaxation of any compressed soft tissue of the plantar surface and to allow any slight modifications of the fluid pattern to compensate for this condition. The feet and legs are maintained in this position until the material is set.

22. The envelopes 12 are now removed from the shoes. The injection pocket 24 and overflow chambers 26 are cut off along the cut line 27 and along neck 40 respectively. The vinyl sheet 37 (forming the stiffener pocket) is removed, the lower layer 16 may also be removed from both heel positioning and arch support chambers 20, 22.

The finished support insert 10 comprises a reinforced upper layer 14, molded in two discrete parts to form a properly conforming heel positioning section 52 and a properly conforming arch support section 54. See FIGS. 3 and 4. Specifically, the finished insole support comprises the reinforced upper sheet 14, a discrete heel positioner support section 52 formed of molded (in situ) plastic, e.g., silicone rubber, affixed to the upper sheet 14, and a discrete arch support section, also formed of molded-in-place plastic (e.g., silicone rubber) and affixed to the said upper sheet. Both the heel support section and the arch support section are separated by the weld line 19, which is essentially free of the molded plastic material.

It will also be understood that the heel positioner and support section 52 could be separately formed completely independently of the arch support section 54. In this case, the heel section 52 once formed, could be then affixed to a separate larger sheet or envelope, for the molding of the arch support section 54. The method and means described with reference to FIGS. 1–4 are presently preferred, however.

Modifications of this invention may be made which lie within the scope of this invention, as in modifying techniques and materials. I intend, therefore, to be bound only by the claims which follow.

I claim:

1. The method of forming a molded arch support insert insole for footwear comprising: introducing a first quantity of room-temperature-curing polymer composition into a first flexible, impervious, pocket member, said first pocket member corresponding to a heel portion of said insole; positioning a heel of a person on said first pocket member while allowing said first quantity to cure, to form a heel positioning support portion of said insole; then introducing a second quantity of said composition into a second flexible, impervious pocket member corresponding to an arch support portion of said insole; curing said second quantity of said composition, while pressing a portion of a foot of said person on said second pocket member and while positioning a heel of said foot on said heel positioning support portion of said insole, to mold said second quantity of said composition to the shape of adjacent portions of said foot, said first and second pocket members being connected at least during the curing of said second quantity of said composition, thereby forming said molded arch support insert insole.

2. The method of claim 1 wherein said heel positioning support portion is held in a predetermined position during molding of said heel positioning support portion.

3. The method of claim 1 wherein just prior to the molding of the said heel positioning support portion and said arch support portion, air is removed from each of said support portions.

4. The method of claim 1 wherein the molding in situ, of said arch support insole, is performed with said person in a standing position and body weight distributed between both feet of said person.

5. The method of claim 1 wherein the molding, in situ, of said heel positioning support portion is performed with the foot of said person being placed in a predetermined position for corrective purposes.

6. The method of claim 1 wherein the molding, in situ, of said arch support insole is performed with the foot of said person being placed in a predetermined position for corrective purposes.

7. The method of claim 1 wherein a predetermined amount of molding composition is employed to mold said heel positioning support portion.

8. The method of claim 1 wherein an excess of molding composition is employed to mold said arch support portion and said excess molding composition is expelled from said arch support portion prior to the curing of said molding composition therein.

9. The method of claim 1 wherein said heel positioning support portion includes a heel stiffening member for equalizing distribution of molding compound in said heel positioning support portion.

10. The method of claim 9 wherein said heel stiffening member is removed after completion of the molding of said heel positioning support portion.

11. The method of forming an arch support insole for footwear comprising: introducing room-temperature-curing polymer composition in a first pocket portion of an impervious envelope having plural pockets, placing a heel of a person on said first pocket portion and only placing part of his weight on said heel; curing said polymer to form a heel positioning support member; then introducing a further portion of said polymer in a second pocket portion of said envelope; pressing a foot of said person on said envelope while positioning said foot on said heel positioning support member, the foot also being placed in a predetermined position for corrective purposes, and curing said further portion of polymer to form said insole support member during said pressing.

12. The method of claim 11 wherein a predetermined amount of molding composition is employed to mold said heel positioning support portion.

13. The method of claim 11 wherein an excess of molding composition is employed to mold said second pocket portion and said excess molding composition is expelled from said arch support member prior to the curing of said molding composition therein.

* * * * *